United States Patent [19]

Hill et al.

[11] Patent Number: 5,728,842
[45] Date of Patent: Mar. 17, 1998

[54] SUBSTITUTED IMIDAZOLYL-ALKYLTHIO-ALKANOIC ACIDS

[75] Inventors: David Taylor Hill, North Wales; Joseph Weinstock, Phoenixville; John Gerald Gleason, Downingtown, all of Pa.

[73] Assignee: SmithKline Beecham Corporation, Philadelphia, Pa.

[21] Appl. No.: 351,443

[22] PCT Filed: Jun. 30, 1993

[86] PCT No.: PCT/US93/06246

§ 371 Date: Feb. 22, 1995

§ 102(e) Date: Feb. 22, 1995

[87] PCT Pub. No.: WO94/00120

PCT Pub. Date: Jan. 6, 1994

[30] Foreign Application Priority Data

Jun. 30, 1992 [GB] United Kingdom ............... 9213934

[51] Int. Cl.$^6$ .............. C07D 233/60; C07D 233/84; C07D 235/02; C07D 403/06; C07D 403/04; A61K 31/415

[52] U.S. Cl. .............. 548/319.1; 514/397; 514/398; 514/399; 514/400; 548/321.1; 548/341.5; 548/342.1; 548/342.5

[58] Field of Search .............. 548/319.1, 321.1, 548/341.5, 342.1, 342.5; 514/397, 398, 399, 400

[56] References Cited

U.S. PATENT DOCUMENTS

| | | | |
|---|---|---|---|
| 4,668,794 | 5/1987 | Wareing, I | 514/400 |
| 4,808,607 | 2/1989 | Wareing, II | 514/400 |
| 5,011,851 | 4/1991 | Meanwell | 514/400 |

FOREIGN PATENT DOCUMENTS

| | | | |
|---|---|---|---|
| 0427463 | 5/1991 | European Pat. Off. | 514/400 |
| 3306646 | 8/1984 | Germany | 514/400 |
| 62-265270 | 11/1987 | Japan | 514/400 |
| 63-141969 | 6/1988 | Japan | 514/400 |
| WO92/02510 | 2/1992 | WIPO | 548/319.1 |
| 92-004330 | 3/1992 | WIPO | 514/400 |
| WO94/00120 | 1/1994 | WIPO | 548/319.1 |

*Primary Examiner*—Floyd D. Higel
*Attorney, Agent, or Firm*—Mary E. McCarthy; Stephen A. Venetianer; Edward T. Lentz

[57] ABSTRACT

Angiotensin II receptor antagonists having the formula:

$$R^2-X-\underset{N}{\underset{\|}{\overset{N-(CH_2)_p-R^1}{\overset{\|}{C}}}}-(CH_2)_q-\left[\underset{R^4}{\overset{}{CH}}\right]_t-S-R^5$$

which are useful in regulating hypertension and in the treatment of congestive heart failure, renal failure, and glaucoma, pharmaceutical compositions including these antagonists, and methods of using these compounds to produce angiotensin II receptor antagonism in mammals.

5 Claims, No Drawings

SUBSTITUTED IMIDAZOLYL-ALKYLTHIO-ALKANOIC ACIDS

This application is a 371 of PCT/U.S. 93/06246 filed Jun. 30, 1993.

The present invention relates to new compounds which are angiotensin II receptor antagonists and are useful in regulating hypertension induced or exacerbated by angiotensin II, and in the treatment of congestive heart failure, renal failure, and glaucoma. This invention also relates to pharmaceutical compositions containing these compounds and methods for using these compounds as antagonists of angiotensin II, as antihypertensive agents and as agents for treating congestive heart failure, renal failure, and glaucoma.

BACKGROUND OF THE INVENTION

The class of peptide pressor hormone known as angiotensin is responsible for a vasopressor action that is implicated in the etiology of hypertension in man. Inappropriate activity of the renin-angiotensin systems appears to be a key element in essential hypertension, congestive heart failure and in some forms of renal disease. In addition to a direct action on arteries and arterioles, angiotensin II (AII), being one of the most potent endogenous vasoconstrictors known, exerts stimulation on the release of aldosterone from the adrenal cortex. Therefore, the renin-angiotensin system, by virtue of its participation in the control of renal sodium handling, plays an important role in cardiovascular hemeostasis.

Interruption of the renin-angiotensin system with converting enzyme inhibitors, such as captopril, has proved to be clinically useful in the treatment of hypertension and congestive heart failure (Abrams, W. B., et al., (1984), *Federation Proc.*, 43, 1314). The most direct approach towards inhibition of the renin-angiotensin system would block the action of AII at the receptor. Compelling evidence suggests that AII also contributes to renal vasoconstriction and sodium retention that is characteristic of a number of disorders such as heart failure, cirrhosis and complications of pregnancy (Hollenberg, N. K., (1984), *J. Cardiovas. Pharmacol.*, 6, S176). In addition, recent animal studies suggest that inhibition of the renin-angiotensin system may be beneficial in halting or slowing the progression of chronic renal failure (Anderson, S., et al., (1985), *J. Clin. Invest.*, 76, 612). Also, a recent patent application (South African Patent Application No. 87/01,653) claims that AII antagonists are useful as agents for reducing and controlling elevated intraocular pressure, especially glaucoma, in mammals.

The compounds of this invention inhibit, block and antagonize the action of the hormone AII, and are therefore useful in regulating and moderating angiotensin induced hypertension, congestive heart failure, renal failure and other disorders attributed to the actions of AII. When compounds of this invention are administered to mammals, the elevated blood pressure due to AII is reduced and other manifestations based on AII intercession are minimized and controlled. Compounds of this invention are also expected to exhibit diuretic activity.

Recognition of the importance of blocking and inhibiting the actions of AII has stimulated other efforts to synthesize antagonists of AII. The following references have disclosed imidazole derivatives which are described as having AII blocking activity and useful as hypotensive agents.

Furukawa et al., U.S. Pat. No. 4,340,598 discloses imidazol-5-yl-acetic acids and imidazol-5-yl-propanoic acids. Specifically, the discloser includes 1-benzyl-2-n-butyl-5-chloroimidazole-4-acetic acid and 1-benzyl-2-phenyl-5-chloroimidazole-4-propanoic acid.

Furukawa, et al., U.S. Pat. No. 4,355,040 discloses substituted imidazole-5-acetic acid derivatives. A compound specifically disclosed is 1-(2-chlorobenzyl)-2-n-butyl-4-chloroimidazole-5-acetic acid.

Carini et al., in European Patent Application Number 253,310 disclose certain substituted imidazoles. An intermediate described in this patent is ethyl 3-[1-(4-nitrobenzyl)-2-butyl-4-chloroimidazol-5-yl]propenoate.

Carini et al., in European Patent Application Number 324,377 disclose substituted imidazoles and processes for their preparation. This application also relates to pharmaceutical compositions containing the substituted imidazoles alone and in conjunction with other drugs, particularly in conjunction with diuretics and non-steroidal antiinflammatory drugs.

DESCRIPTION OF THE INVENTION

The compounds of the present invention that are blockers of angiotensin II receptors are represented by the following Formula (I):

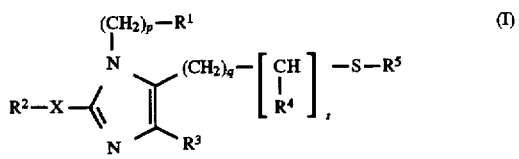

in which:

R¹ is adamantyl, phenyl, biphenyl, or naphthyl, with each phenyl, biphenyl, or naphthyl group being unsubstituted or substituted by one to three substituents selected from Cl, Br, F, I, $C_1$–$C_6$alkyl, nitro, A—$CO^2R^7$, tetrazol-5-yl, $C_1$–$C_6$alkoxy, hydroxy, $SC_1$–$C_6$alkyl, $SO_2NHR^7$, $NHSO_2R^7$, $SO_3H$, $CONR^7R^7$, CN, $SO_2C_1$–$C_6$alkyl, $NHSO_2R^7$, $PO(OR^7)_2$, $NR^7R^7$, $NR^7COH$, $NR^7COC_1$–$C_6$alkyl, $NR^7$ $CON(R^7)_2$, $NR^7COY$, Y, or $SO_2Y$;

R² is $C_2$–$C_{10}$alkyl, $C_3$–$C_{10}$alkenyl, $C_3$–$C_{10}$alkenyl, $C_3$–$C_6$cycloalkyl, or $(CH_2)_{0-8}$phenyl unsubstituted or substituted by one to three substituents selected from $C_1$–$C_6$alkyl, nitro, Cl, Br, F, I, hydroxy, $C_1$–$C_6$alkoxy, $NR^7R^7$, $CO_2R^7$, CN, $CONR^7R^7$, Y, tetrazol-5-yl, $NR^7COC_1$–$C_6$alkyl, $NR^7$ COY, $SC_1$–$C_6$alkyl, $SO_2Y$, or $SO_2C_1$–$C_6$alkyl;

X is a single bond, S, or O;

R³ is hydrogen, Cl, Br, F, I, CHO, hydroxymethyl, $COOR^7R^7$ $CONR^7R^7$, $NO_2$, Y, CN, $NR^7R^7$, or phenyl;

Y is $C_mF_{2m+1}$;

A is —$(CH_2)_p$—, —CH=CH—, —$O(CH_2)_m$—, or —$S(CH_2)_m$;

R⁴ is H, $C_1$–$C_6$alkyl, or —$S(CH_2)_{1-4}CO_2R^7$;

t is 0 or 1;

R⁵ is —$CHR^6(CH_2)_qCO_2R^7$ or —$(CH_2)_nR^9$;

R⁶ is hydrogen, $CO_2R^7$, $C_1$–$C_6$alkyl, or —$(CH_2)_nR^8$;

each m independently is 1–3;

each n independently is 1–3;

each p independently is 0–4;

each q independently is 0–2;

each R⁷ independently is hydrogen or $C_1$–$C_6$alkyl;

R⁸ is phenyl, naphthyl, 2- or 3-thienyl, 2- or 3-thiazolyl, triazolyl, tetrazolyl, pyrazolyl, pyrrolyl, oxazolyl, or isoxazolyl, with each $R^8$ group being unsubstituted or substituted by $C_1$–$C_6$alkyl, $C_1$–$C_6$alkoxy, Cl, Br, F, I, $NR^7R^7$, $CONR^7R^7$, $CO_2R^7$, $SO_3H$, $SO_2NHR^7$, OH, $NO_2$, Y, $SO_2C_1$–$C_6$alkyl, $SO_2Y$, $SC_1$–$C_6$alkyl $NR^7COH$, $NR^7COY$, or $NR^7COC_1$–$C_6$alkyl; and $R^9$ is phenyl, naphthyl, 2- or 3-thienyl, 2- or 3-furyl, 2-, 3-, or 4-pyridyl, pyrimidyl, imidazolyl, thiazolyl, triazolyl, tetrazolyl, pyrazolyl, pyrrolyl, oxazolyl, or isoxazolyl, with each $R^9$ group being unsubstituted or substituted by $C_1$–$C_6$alkyl, $C_1$–$C_6$alkoxy, Cl, Br, F, I, $NR^7R^7$, $CO_2R^7$, $CONR^7R^7$, $SO_3H$ $SO_2NHR^7$, OH, $NO_2$, Y, $SO_2C_1$–$C_6$alkyl, $SO_2Y$, $SC_1$–$C_6$alkyl, $NR^7COH$, $NR^7COY$, or $NR^7COC_1$–$C_6$alkyl; or a pharmaceutically acceptable salt thereof.

Preferred compounds of this invention are represented by Formula (I) when:

$R^1$ is phenyl or naphthyl, with each phenyl or naphthyl group being unsubstituted or substituted by one to three substituents selected from Cl, Br, F, $CF_3$, $NO_2$, $C_1$–$C_6$alkyl, $C_1$–$C_6$alkoxy, hydroxy, A—$CO_2R^7$, $CONR^7R^7$, or tetrazol-5-yl;

each p independently is 0–2;

X is a single bond or S;

$R^2$ is $C_2$–$C_8$alkyl;

$R^3$ is hydrogen, Cl, F, $CF_3$, or $NO_2$;

$R^5$ is —$CHR^6(CH_2)_q$ $CO_2R^7$ in which $R^6$ is hydrogen, $CO_2R^7$, $C_1$–$C_6$alkyl, or $(CH_2)_nR^8$, wherein $R^8$ is phenyl, naphthyl, 2- or 3-thienyl, or 2- or 3-furyl, with each $R^8$ group being unsubstituted or substituted by $C_1$–$C_6$alkyl or $C_1$–$C_6$alkoxy; or —$(CH_2)_nR^9$ in which $R^9$ is phenyl or 2-, 3-, or 4-pyridyl with each $R^9$ group being substituted by $CO_2R^7$, or $R^9$ is imidazolyl; or a pharmaceutically acceptable salt thereof.

As used herein, the terms alkyl, alkenyl, alkoxy and alkynyl mean carbon chains which are branched or unbranched with the length of the chain determined by the descriptor preceding the term.

Particular compounds of the invention include, but are not limited to, the following:

S-[(2-n-butyl-1-{(4-carboxyphenyl)methyl}-1H-imidazol-5-yl)methyl]-D,L-2-thio-3-(2-thienyl) propenoic acid, S-[(2-n-butyl-1-{(4-carboxyphenyl)methyl}-1H-imidazol-5-yl)methyl]thiogylcolic acid, S-[(2-n-butyl-1-{(4-carboxyphenyl)methyl}-1H-imidazol-5-yl)methyl]thiolactic acid, S-[(2-n-butyl-1-{(4-carboxyphenyl)methyl}-1H-imidazol-5-yl)methyl]-3-thiopropionic acid, S-[(2-n-butyl-1-{(4-carboxyphenyl)methyl}-1H-imidazol-5-yl)methyl]mercaptosuccinic acid, 5-[2-n-butyl-1-{(4-carboxyphenyl)methyl}-1H-imidazol-5-yl]-4,6-dithianonane-1, 9-dioic acid, 5-[(2-n-butyl-1-{(4-carbomethoxyphenyl)methyl}-1H-imidazol-5-yl)methyl]-2-thio-3-(2-thienyl) propionic acid, S-[(2-n-butyl-1-{(4-carboxyphenyl)methyl}-1H-imidazol-5-yl)methyl]-D-2-thio-3-phenylpropionic acid, S-[(2-n-butyl-1-{(4-carboxyphenyl)methyl}-1H-imidazol-5-yl)methyl]-L-2-thio-3-phenylpropionic acid, S-[(2-n-butyl-1{(4-carboxyphenyl)methyl}-1H-imidazol-5-yl)methyl]thiosalicylic acid, S-[(2-n-butyl-2-{(4-carboxyphenyl)methyl}-1H-imidazol-5-yl)methyl]-2-mercaptonicotinic acid, 4-[(2-n-butyl-5-{[(2-carboxyphenyl)thio]methyl}-1H-imidazol-5-yl)methyl]-1-naphthalenecarboxylic acid, methyl 4-[(2-n-butyl-5-{[(2-carbomethoxyphenyl)-thio] methyl}-1H-imidazol-5-yl)methyl]-1-naphthalenecarboxylate, S-[(2-n-butyl-1-{(4-carboxyphenyl)methyl}-4-chloro-1H-imidazol-5-yl)methyl]thiosalicylic acid, S-[(2-n-butyl-1-{(4-carboxyphenyl)methyl}-1H-imidazol-5-yl)methyl]-4-thiobenzoic acid, S-[(2-n-butyl-1-{(4-carboxyphenyl)methyl}-1H-imidazol-5-yl)methyl]-3-thiobenzoic acid, S-[(2-n-butyl-1-{(4-carbomethoxyphenyl)methyl}-1H-imidazol-5-yl)methyl]-2-thioimidazole, 5 S-[(2-n-butyl-1-{(4-carboxyphenyl)methyl}-4-nitro-1H-imidazol-5-yl)methyl]thiosalicylic acid, S-[(2-n-butyl-1-{(4-carboxyphenyl)methyl}-1H-imidazol-5-yl]thiosalicylic acid, S-[(2-n-butyl-1-{(4-carboxyphenyl)methyl}-1H-imdazole-5-yl]ethyl-thiosalicylic acid, S-[2-(2-n-butyl-1-{(4-carboxyphenyl)methyl}-1H-imidazol-5-yl) ethyl]thiosalicyclic acid, S-[(2-n-butyl-1-{(4-carboxyphenyl)methyl}-4-nitro-1H-imidazol-5-yl)methyl|mercaptoacetic acid, and S-[(2-n-butyl-1-{(4-carboxyphenyl)methyl}-4-nitro-1H-imidazol-5-yl)methyl]-L-2-thio-3-phenylpropionic acid; or a pharmaceutically acceptable salt thereof.

The most preferred compounds of this invention are:

S-[(2-n-butyl-1-{(4-carboxyphenyl)methyl}-1H-imidazol-5-yl)methyl]-2-thio-3-(2-thienyl) propenoic acid, S-[(2-n-butyl-1-{(4-carboxyphenyl)methyl}-1H-imidazol-5-yl)methyl]thiosalicylic acid, S-[(2-n-butyl-1-{(4-carboxyphenyl)methyl}-1H-imidazol-5-yl)methyl]-2-mercaptonicotinic acid, 4-[(2-n-butyl-5-{[(2-carboxyphenyl)thio]methyl}-1H-imidazol-5-yl)methyl]-1-naphthalenecarboxylic acid; or a pharmaceutically acceptable salt thereof.

The invention also relates to pharmaceutical compositions comprising a pharmaceutical carrier and an effective amount of a compound of Formula (I).

Also included in the present invention are methods for antagonizing angiotensin II receptors which comprises administering to a subject in need thereof an effective amount of a compound of Formula (I). Methods of treating hypertension, congestive heart failure, glaucoma, and renal failure by administering these compounds are also included in this invention.

The angiotensin II receptor antagonizing compounds are also of value in the treatment of left ventricular hypertrophy regression, diabetic nephropathy, diabetic retinopathy, mascular degeneration, haemorrhagic stroke, primary and secondary prevention of infarction, prevention of atheroma progression and the regression of atheroma, prevention of restinosis after angioplasty or bypass surgery, improving cognitive function, angina, and CNS disorders, such as anxiety.

The compounds of this invention are prepared by procedures described herein and illustrated by the examples. Reagents, protecting groups and functionality on the imidazole and other fragments of the molecule must be consistent with the proposed chemical transformations. Steps in the synthesis must be compatible with the functional groups and the protecting groups on the imidazole and other parts of the molecule.

The following procedures are useful for the preparation of Formula (I) compounds particularly where $R^1$ is 4-carboxyphenyl, p is one, $R^2$ is n-propyl or n-butyl, X is S or a single bond, or $R^3$ is hydrogen, Cl, F, $NO_2$, or $CF_3$.

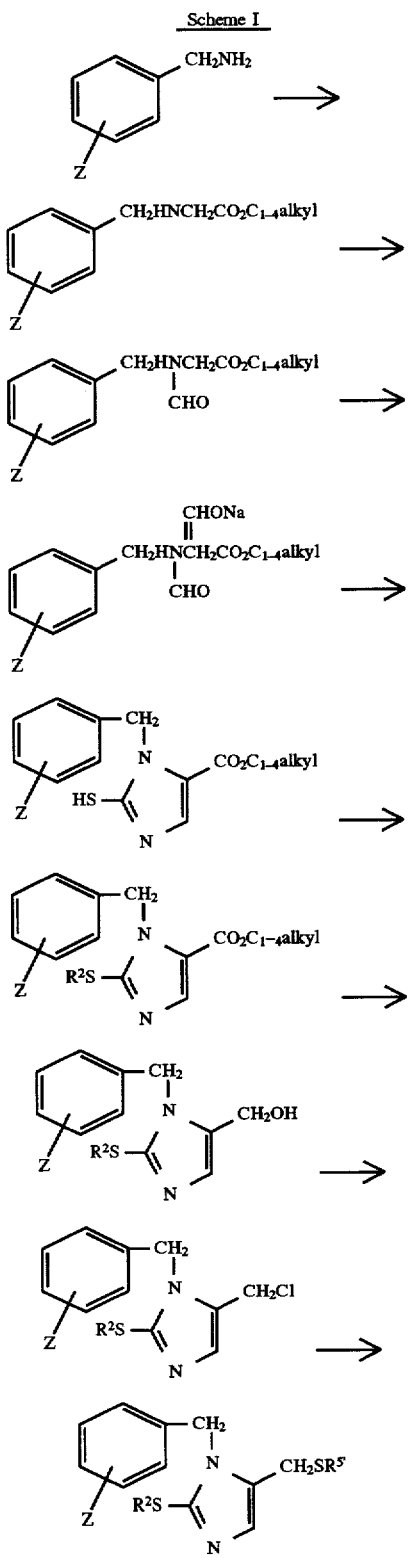

Scheme I outlines the synthesis of Formula (I) compounds in which the 2-position substituent is $R^2S$. Benzylamines (1), unsubstituted or substituted by one to three Z substituents selected from halo, $C_1$–$C_6$alkyl, $SO_2C_1$–$C_6$alkyl, $C_1$–$C_6$alkoxy, CN, $NO_2$, $CO_2C_1$–$C_4$alkyl, $SC_1$–$C_6$alkyl, or $C_nF_{2n+1}$, wherein n is 1–3, are alkylated with a $C_1$–$C_6$alkyl chloroacetate, for example, methyl chloroacetate, in the presence of a base, such as triethylamine, in a suitable solvent, such as dimethylformamide. The resulting alkylaminoalkyl ester compounds (2) are N-formylated with formic acid in the presence of a suitable solvent, such as xylene, to give formula (3) compounds. Formula (4) compounds are formed by C-formylation of the carbon alpha to both the amino and the ester groups of the formula (3) compounds in a reaction with an alkyl formate, such as methyl formate, in the presence of an alkali metal halide, such as sodium hydride, in a suitable solvent, such as tetrahydrofuran. Reaction of this intermediate with acidic thiocyanate, preferably potassium thiocyanate, in an inert organic solvent, such as $C_{1-4}$alkanol, produces formula (5) 1-$R^1CH_2$-2-mercapto-5-alkanoate ester imidazoles. The free thio group of formula (5) compounds is reacted with a halo-$R^{10}$ compound, wherein $R^{10}$ is $C_{2-10}$ alkyl, $C_{3-10}$ alkenyl, $C_{3-6}$ cycloalkyl, or an optionally substituted ($CH_2$)$_{0-8}$ phenyl, preferably propyl bromide, in the presence of a suitable base, such as sodium carbonate, in an appropriate solvent, such as ethyl acetate, to give 1-$R^1CH_2$-2-$R^2$S-5-alkanoate ester imidazoles (6). The hydroxymethyl imidazoles of formula (7) are prepared from formula (6) compounds by reduction with an appropriate reagent, such as diisobutyl aluminum hydride, in a suitable solvent, such as tetrahydrofuran, at a temperature of about −78° C. to about 25° C., preferably at about −10° C. The formula (8) chloromethyl compounds are prepared by reacting formula (7) hydroxymethyl compounds with a halogenating agent, such as refluxing thionyl chloride. Reaction of formula (8) compounds with an appropriately substituted mercaptan, $HSR^{5'}$, wherein $R^{5'}$ is $-CHR^6(CH_2)_qCO_2C_1$–$C_6$alkyl, in which $R^{6'}$ is hydrogen, $CO_2C_{1-6}$alkyl, $C_1$–$C_6$alkyl, or $-(CH_2)_nR^{8'}$ wherein $R^{8'}$ is as defined for $R^8$ except $R^{8'}$ is not substituted by $CONR^7R^7$, $CO_2H$, or OH, or wherein $R^{5'}$ is $-(CH_2)_nR^{9'}$ in which $R^{9'}$ is as defined for $R^9$ except $R^{9'}$ is not substituted by $CONR^7R^7$, $CO_2H$, or OH, in the presence of a base, such as triethylamine, in a suitable solvent, such as dimethylformamide, at a temperature from about 30° C. to about 70° C., preferably from about 25° C. to about 60° C. Formula (I) compounds wherein $R^8$ or $R^9$ are substituted by $CO_2H$, or $R^6$ is $CO_2H$, or $R^5$ is $-CHR^6(CH_2)_qCO_2H$ are prepared from the corresponding $CO_2C_{1-6}$alkyl compounds using aqueous base, such aqueous sodium carbonate solution or aqueous sodium or potassium hydroxide solution, in a suitable organic solvent, such as methanol or ethanol.

Formula (I) compounds wherein $R^8$ and $R^9$ are substituted by $CONR^7R^7$ are prepared from the Formula (I) compounds wherein $R^8$ and $R^9$ are substituted by $CO_2H$. These carboxylic acid compounds are converted to the corresponding acid halide derivatives using, for example, thionyl chloride. The acid halide intermediate is then reacted with an appropriately substituted amine, $HNR^7R^7$, to give the Formula (I) compounds wherein $R^8$ or $R^9$ are substituted by $CONR^7R^7$.

Formula (I) compounds wherein $R^8$ and $R^9$ are substituted by OH are prepared from the Formula (I) compounds wherein $R^8$ or $R^9$ are substituted by $C_1$–$C_4$alkoxy using an ether-cleaving reagent, such as boron tribromide or hydrobromic acid.

Scheme II

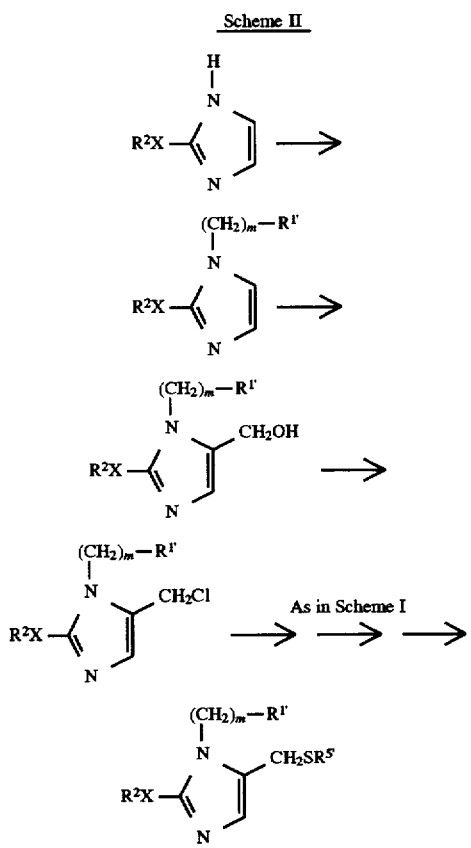

Formula (I) compounds are also prepared by the procedures of Scheme II. The starting 2-R²X-imidazoles of formula (10) are known to the art (J. Org. Chem. 45:4038, 1980) or are synthesized by known procedures. For example, imidazole is converted to 2-n-butylimidazole by reacting imidazole with triethylorthoformate and p-toluenesulfonic acid to give 1-diethoxyorthoamide imidazole and then treating with n-butyl lithium to give the 2-lithium derivative of the orthoamide and alkylating with n-butyl iodide in a suitable solvent, such as tetrahydrofuran.

The 1-R¹'—(CH₂)₁₋₄-group, wherein R¹' is as defined for R¹ except R¹' is not substituted by A—CO₂H, tetrazol-5-yl, hydroxy, or CONR⁷R⁷, is incorporated onto the 2-R²X-imidazole of formula (10)by known procedures, for example, by reaction with a R¹'-(CH₂)₁₋₄ halide, mesylate or acetate, such as 2-chlorobenzyl bromide or 4-carbomethoxybenzyl bromide, in a suitable solvent, such as dimethylformamide, in the presence of a suitable acid acceptor, such as sodium alkylate, potassium or sodium carbonate, or a metal hydride, preferably sodium hydride, at a reaction temperature of about 25° C. to about 100° C., preferably at about 50° C. The resulting formula (11) imidazole is hydroxymethylated in the 5-position, for example, by reacting with formaldehyde in the presence of sodium acetate in acetic acid to provide the 1-R¹'-(CH₂)₁₋₄-2-R²X-5-hydroxymethylimidazole intermediates of formula (12). Chloromethyl formula (13) compounds are prepared from formula (12) hydroxymethyl imidazoles in a reaction with a halogenating agent, for example, refluxing thionyl chloride. Formula (I) compounds are prepared from the chloromethyl imidazoles by the methods described in Scheme I.

Alternatively, the 1-R¹'-(CH₂)₁₋₄-2-R²X-5-hydroxymethylimidazole intermediates of formula (12) are prepared by reacting an aimido ether, R²X—C(=NH)—O-alkyl, such as valeramidine methyl ether, or an amidine, such as valeramidine, with dihydroxyacetone in liquid ammonia under pressure to give 2-R²X-5-hydroxymethylimidazole. This intermediate is reacted with acetic anhydride to give 1-acetyl-5-acetoxymethyl-2-R²X-imidazole. The diacetate intermediate is N-alkylated, for example, using 2-chlorobenzyl triflate or 4-carbomethoxybenzyl triflate, and the resulting 1-R¹'-(CH₂)₁₋₄-2-R²X-5-acetoxymethylimidazole is de-protected using conventional acetate ester cleaving techniques, such as treatment with aqueous base, for example aqueous sodium hydroxide solution, to give the 1-R¹'(CH₂)₁₋₄-2-R²X-5-hydroxymethylimidazole intermediate of formula (12). Formula (I) compounds are prepared from the hydroxy-methylimidazoles by the procedures detailed above.

Alternatively, Formula (I) compounds are prepared by the following procedure. Starting 2-R²X-imidazol-5-carboxaldehydes, prepared by the oxidation of the 2-R²X-5-hydroxymethylimidazoles described hereinbefore, are reacted with an N-alkylating protecting reagent, such as chloromethyl pivalate (POM-Cl), in the presence of a base, such as potassium carbonate, in a suitable solvent, such as dimethylformamide, at a temperature of about 20° C. to about 50° C., preferably at about 25° C., to give N-alkylation (e.g., POM-derivation) on the least hindered nitrogen atom of the imidazole nucleus. The 1-R¹'-(CH₂)₁₋₄-group is incorporated onto the imidazole by N-alkylation of the above prepared aldehyde with a halomethylbenzene compound, such as methyl 4-bromomethylbenzoate, at a temperature of about 80° C. to about 125° C., preferably at about 100° C. The protecting group on the 3-nitrogen of the imidazole ring is removed by base hydrolysis, for example using a biphasic mixture of ethyl acetate and aqueous sodium carbonate, to give 1-R¹'CH₂-2-R²X-imidazole-5-carboxaldehyde compounds. The Formula (I) compounds can be prepared from these 5-carboxaldehyde compounds by the methods described above.

The 1-R¹'—(CH₂)₁₋₄-2-R²X-5-hydroxymethyl imidazole intermediates, wherein R³ is H, Cl, Br, or I, are prepared in the following manner. The 2-R²X-5-hydroxyimidazole compounds, hereinbefore described, are treated with a N-halosuccinimide, such as bromo-, iodo- or chlorosuccinimide, in a suitable solvent at a reaction temperature from about 30° C. to about 80° C., preferably from about 40° C. to about. 60° C. The 5-hydroxymethyl group is then oxidized to the corresponding 5-carboxaldehyde derivative using a suitable oxidizing agent, such as manganese dioxide, in an inert solvent, for example in methylene chloride, at a temperature of about 25° C. to about 40° C., preferably at about 40° C. The —R¹'—(CH₂)₁₋₄-group, wherein R¹' is as defined previously, is incorporated onto the 2-R²X-4-haloimidazol-5-carboxaldehydes by known proceedures, for example, by reaction with R¹'—(CH₂)₁₋₄-halide, such as methyl 4-bromomethylnaphthalene-1-carboxylate or methyl 4-bromomethylbenzoate, in a suitable solvent, such as dimethylformamide, in the presence of a suitable base such as potassium carbonate at a temperature of about 40° C. to about 100° C., preferably at about 60C. The 4-halo group may be removed catalytically, for example, by using palladium on carbon in the presence of hydrogen and anhydrous potassium acetate in a suitable solvent, such as in methanol, or, in the alternative, the halo group may be retained on the imidiazole nucleus to prepare the Formula (I) compounds using the methods hereinbefore described.

Compounds wherein the R¹' group is directly attached to the nitrogen of the imidazole ring are prepared following methods described in U.S. Pat. No. 4,194,049. For example, an appropriately substituted benzylamine is reacted with a $R^{1'}$-nitrile, such as valeronitrile, in the presence of a Lewis Acid, such as zinc chloride or aluminum chloride, in an inert organic solvent, such as tetrahydrofuran, methylene chloride, or toluene, at a temperature of about 25° C. to about 150° C. The resulting amidine is converted to the 1-$R^{1'}$-2-$R^2$X-imidazol-5-carboxaldehyde derivative in a reaction with a halomalonaldehyde, such as bromomalonaldehyde, in an appropriate solvent, such as a $C_1$-$C_4$alkyl alcohol. The 5-hydroxymethylimidazole is prepared by reacting the 5-carboxaldehyde compound with a metal hydride reducing agent, such as sodium borohydride, in an organic solvent, such as $C_1$-$C_4$alkyl alcohol. The Formula (I) compounds are prepared form these alcohol intermediates using the methods described in Scheme I.

Formula (I) compounds wherein the alkylene bridge at the 5 position of the imidazole reing is defined as q equal to 0 are prepared as follows. The formula (10), Scheme II, imidazoles are reacted with a halogenating agent, such as N-bromosuccinimide, in a suitable solvent, such as carbon tetrachloride, at a temperature of about 40° C. to about 60° C., preferably at about 60° C., to give the 2-$R^2$X-4,5-dihaloimidazole intermediate. This di-halo compound is converted to the 2-$R^2$X-4-haloimidazole, compound such as 2-n-butyl-4-bromoimidazole, in a reaction with sodium sulfite. Nitration of this intermediate using, for example, nitric acid and sulfuric acid, gives 2-$R^2$X-5-halo-4-nitroimidazoles. The 1-$R^{1'}$-$(CH_2)_{1-4}$-group$_p$, wherein $R^1$ is as defined previously, is incorporated onto the 2-$R^2$X-5-halo-4-nitroimidazoles by known procedures, for example, by reaction with a $R^{1'}$-$(CH_2)_{1-4}$-halide, such as methyl 4-bromomethylbenzoate, in a suitable solvent, such as dimethylformaide, in the presence of a suitable base, such as potassium carbonate, at a temperature of about 40° C. to about 100° C. The 5-halo group is displaced by HSR$^{5'}$, wherein R$^{5'}$ is as defined for $R^5$ except $R^{5'}$ is not substituted by $CO_2H$, tetrazol-5-yl, hydroxy, or CONR$^7R^7$, in the presence of a base, such as lithium diisopropylamine, in a suitable solvent, such as tetrahydrofuran, at a temperature from about −78° C. to about 25° C. to give Formula (I) 1-$R^{1'}$-$(CH_2)_{1-4}$-2-$R^2$X-4-$NO_2$-5-SR$^{5'}$-imidazoles. The 4-$NO_2$ compound may be converted the corresponding 4-H compound by reacting the nitro group with sodium hydrosulfide to give the 4-$NH_2$ compound, which is subsequently de-aminated, for example, by using sodium nitrate in the presence of a suitable solvent, such as a mixture of hydrochloric acid, hypophosphorus acid and water, at a temperature from about −10° C. to about 10° C., preferably at 0° C.

Formula (I) compounds wherein the alkylene bridge at the 5-position of the imidazole ring is defined as q equal to 2 are prepared as follows. The 1-$R^{1'}$-$(CH_2)_{1-4}$-2-$R^2$X-5-hydroxyethylimidazole intermediates are prepared by reacting an amidine, $R^2$X—C(=NH)NH$_2$, such as valeramide, with methyl 3-formylacrylate to give 2-$R^2$X-5-carbomethoxymethyl-imidazole compounds. The ester group is reduced to the corresponding alcohol using a suitable reagent, such as lithium aluminum hydride, in a suitable solvent, such as tetrahydrofuran. The Formula (I) compounds wherein q is 2 are prepared from the 2$R^2$X-5-imidazol-ethanol compounds using the methods hereinbefore described.

Alternately, Formula (I) compounds wherein the alkylene bridge at the 5 position of the imidazole ring is defined as q equal to 2 are prepared from the corresponding alkanoic esters, which are disclosed in U.S. Pat. No. 4,340,598. These ester imidazoles are reduced to the corresponding alcohols using a reducing agent such as lithium alumminum hydride, in an inert solvent, such as tetrahydrofuran. The Formula (I) compounds are prepared from these alcohol intermediates using the methods described in Scheme I.

The compounds of the Formula (I) wherein $R^4$ is —S$(CH_2)_{1-4}CO_2R^7$ are conveniently prepared by forming the dithioacetal derivatives of 1-$R^{1'}$-$(CH_2)_{1-4}$-2-$R^2$-X-imidazole-5-carboxaldehydes, prepared hereinbefore, utilizing the appropriate mercaptoalkanoic acids. The reaction of the aldehyde with two equivalents of the mercaptoalkanoic acid is accomplished at about −10° C. to about 20° C., preferably at about 0° C., under acidic conditions in an inert solvent. Examples of such inert solvents include chlorinated hydrocarbons, such as, methylene chloride, chloroform and dichloroethane. The acidic conditions are produced by mineral acids, such as hydrochloric acid and sulfuric acid, or Lewis acids, such as boron trifluoride etherate.

Compounds of Formula (I) in which the $R^1$ substituent or the $R^5$ group is substituted by hydroxy are formed from Formula (I) compounds in which the $R^1$ group is substituted by $C_1$-$C_4$alkoxy using an ether-cleaving reagent, such as boron tribromide or hydrobromic acid.

Compounds of Formula (I) in which the $R^1$ substituent or the $R^5$ group is substituted by carboxy are formed from Formula (I) compounds in which the $R^1$ group is substituted by $CO_2C_1$-$C_4$alkyl using basic hydrolysis, such as aqueous sodium or potassium hydroxide in methanol or ethanol, or using acidic hydrolysis, such as aqueous hydrochloric acid.

Compounds of Formula (I) in which the $R^1$ substituent or the $R^5$ group is substituted by a tetrazol-5-yl group are prepared from the corresponding carboxy compounds. For example, Formula (I) acid compounds are reacted with a halogenating agent, such as thionyl chloride, in a suitable solvent, for example benzene, to give the corresponding acid halide compounds. The acid halides are then converted to primary amide compounds in a reaction with concentrated ammonia, to give Formula (I) compounds in which the $R^1$ substituent is substituted by $CONH_2$. Subsequent dehydration of the amides with oxalyl chloride/dimethylformamide in acetonitrile/dimethylformamide yields the nitrile compounds, which are the immediate precursors to the Formula (I) tetrazole compounds. Tetrazole formation is accomplished by reacting the nitriles with azide, preferably aluminum azide prepared in situ by the reaction of sodium azide with, aluminum chloride, in a suitable solvent, for example tetrahydrofuran.

Compounds of Formula (I) in which the $R^1$ substituent or the $R^5$ group is substituted by CON($C_1$-$C_6$alkyl)$_2$ are prepared from the corresponding carboxy compounds. These carboxylic acid compounds are converted to the corresponding acid halide derivatives using, for example, thionyl chloride. The acid halide intermediate is then reacted with an appropriately substituted amine, HN ($C_1$-$C_6$alkyl)$_2$, to give the Formula (I) amide compounds.

Pharmaceutically acceptable acid addition salts of compounds of Formula (I) are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Representative examples of suitable acids are maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids.

Pharmaceutically acceptable base addition salts of compounds of Formula (I) are prepared by known methods from organic and inorganic bases, including nontoxic alkali metal and alkaline earth bases, for example, calcium, lithium, sodium, and potassium hydroxide; ammonium hydroxide, and nontoxic organic bases, such as triethylamine, butylamine, piperazine, meglumine, choline, diethanolamine, and tromethamine.

Angiotensin II antagonist activity of the compounds of Formula (I) is assessed by in vitro and invivomethods. In vitro antagonist activity is determined by the ability of the compounds to compete with $^{125}$I-angiotensin II for binding to vascular angiotensin II receptors and by their ability to antagonize the contractile response to angiotensin II in the isolated rabbit aorta. In vivo activity is evaluated by the efficacy of the compounds to inhibit the pressor response to exogenous angiotensin II in conscious rats and to lower blood pressure in a rat model of renin dependent hypertension.

Binding

The radioligand binding assay is a modification of a method previously described in detail (Gunther et al., Circ. Res. 47:278, 1980). A particular fraction from rat mesenteric arteries is incubated in Tris buffer with 80 pM of $^{125}$I-angiotensin II with or without angiotensin II antagonists for 1 hour at 25° C. The incubation is terminated by rapid filtration and receptor bound $^{125}$-angiotensin II trapped on the filter is quantitated with a gamma counter. The potency of angiotensin II antagonists is expressed as the $IC_{50}$ which is the concentration of antagonist needed to displace 50% of the total specifically bound angiotensin II. Exemplary of the $IC_{50}$ of compounds of the invention is about 10.0 nM to about 3.0 µM.

Aorta

The ability of the compounds to antagonize angiotensin II induced vasoconstriction is examined in the rabbit aorta. Ring segments are cut from the rabbit thoracic aorta and suspended in organ baths containing physiological salt solution. The ring segments are mounted over metal supports and attached to force displacement transducers which are connected to a recorder. Cumulative concentration response curves to angiotensin II are performed in the absence of antagonist or following a 30-minute incubation with antagonist. Antagonist disassociation constants ($K_B$) are calculated by the dose ratio method using the mean effective concentrations. Exemplary of the $K_B$ of compounds of the invention is about 4.0 nM to about 300 nM.

Inhibition of pressor response to angiotensin II in conscious rats

Rats are prepared with indwelling femoral arterial and venous catheters and a stomach tube (Gellai et al., Kidney Int. 15:419, 1979). Two to three days following surgery the rats are placed in a restrainer and blood pressure is continuously monitored from the arterial catheter with a pressure transducer and recorded on a polygraph. The change in mean arterial pressure in response to intravenous injections of 250 mg/kg angiotensin II is compared at various time points prior to and following the administration of the compounds intravenously or orally at doses of 0.1 to 300 mg/kg. The dose of compound needed to produce 50% inhibition of the control response to angiotensin II ($IC_{50}$) is used to estimate the potency of the compounds. The $IC_{50}$ of S-[(2-n-butyl-1-{(4-carboxyphenyl)methyl}-1H-imidazol-5-yl) methyl]-thiosalicylic acid is about 0.50 mg/kg i.v.

Antihypertensive activity

The antihypertensive activity of the compounds is measured by their ability to reduce mean arterial pressure in conscious rats made renin-dependent hypertensive by ligation of the left renal artery (Cangiano et al., J. Pharmacol. Exp. Ther. 208:310, 1979). Renal artery ligated rats are prepared with indwelling catheters as described above. Seven to eight days following renal artery ligation, the time at which plasma renin levels are highest, the conscious rats are placed in restrainers and mean arterial pressure is continuously recorded prior to and following the administration of the compounds intravenously or orally. The dose of compound needed to reduce mean arterial pressure by 30 mm Hg ($IC_{30}$) is used as an estimate of potency.

The intraocular pressure lowering effects employed in this invention may be measured by the procedure described by Watkins, et al., J. Ocular Pharmacol., 1 (2):161–168 (1985).

The compounds of Formula (I) are incorporated into convenient dosage forms, such as injectable preparations, or for orally active compounds, capsules or tablets. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, such as an ampoule, or an aqueous or nonaqueous liquid suspension.

For topical ophthalmolgic administration, the pharmaceutical compositions adapted include solutions, suspensions, ointments, and solid inserts. Typical pharmaceutically acceptable carriers are, for example, water, mixtures of water and water-miscible solvents such as lower alkanols or vegetable oils, and water soluble ophthalmologically acceptable non-toxic polymers, for example, cellulose derivatives such as methyl cellulose. The pharmaceutical preparation may also contain non-toxic auxiliary substances such as emulsifying, preserving, wetting, and bodying agents, as for example, polyethylene glycols; antibacterial components, such as quarternary ammonium compounds; buffering ingredients, such as alkali metal chloride; antioxidants, such as sodium metabisulfite; and other conventional ingredients, such as sorbitan monolaurate.

Additionally, suitable ophthalmic vehicles may be used as carrier media for the present purpose including conventional phosphate buffer vehicle systems.

The pharmaceutical preparation may also be in the form of a solid insert. For example, one may use a solid water soluble polymer as the carrier for the medicament. Solid water insoluble inserts, such as those prepared from ethylene vinyl acetate copolymer, may also be utilized.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral, parenteral, or topical products.

Doses of the compounds of Formula (I) in a pharmaceutical dosage unit as described above will be an efficacious, nontoxic quantity selected from the range of 0.01–300 mg/kg of active compound, preferably 1–100 mg/kg. The selected dose is administered to a human patient in need of angiotensin II receptor antagonism from 1–6 times daily, orally, rectally, topically, by injection, or continuously by infusion. Oral dosage units for human administration preferably contain from 1 to 500 mg of active compound. Preferably, lower dosages are used for parenteral administration. Oral administration, at higher dosages, however, also can be used when safe and convenient for the patient. Topical formulations contain the active compound in an amount selected from 0.0001 to 0.1 (w/v%), preferably from 0.0001 to 0.01. As a topical dosage unit form, an amount of active compound from between 50 ng to 0.05 mg, preferably 50 ng to 5 mg, is applied to the human eye.

The compounds of this invention may be co-administered with other pharmaceutically active compounds, for example in combination, concurrently or sequentially. Conveniently the compounds of this invention and the other active compound or compounds are formulated in a pharmaceutical composition. Examples of compounds which may be included in pharmaceutical compositions with the compounds of Formula (I) are diuretics, particularly a thiazide diuretic, such as hydrochlorothiazide, or a loop diuretic, such as furosemide, a calcium channel blocker, particularly dihydropyridine antagonists, such as nifedipine, β-adrenoceptor blockers, such as propranolol, renin inhibitors, such as enalkinen, and angiotensin converting enzyme inhibitors, such as captopril or enalapril.

The AII receptor antagonist compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydroahloride, metolazone, metoprolol tartrate, methyclothiazide, methyldopa, methyldopate hydrochloride, minoxidil, pargyline hydrochloride, polythiazide, prazosin, rauwolida serpentina, rescinnaming, sylate, benzithiazide, quinethazone, ticynafan, triamterene, acetazolamide, aminophylline, cyclothiazide, ethacrynic acid, merethoxylline procaine, sodium ethacynate, delapril hydrochloride, enalaprilat, fosinopril sodium, lisinopril, pentopril, quinapril hydrochloride, ramapril, teprotide, zofenopril calcium, diflusinal, diltizem, felodipine, nicardipine, niludipine, minodipine, nisoldipine, nitrenedipine, verapimil and the like, as well as admixtures and combinations thereof. The AII receptor antagonist compounds of this invention can also be administered in combination with a monoamine oxidase inhibitor, such as parnate.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg), chlorothiazide (125–2000 mg), ethacrynic acid (15–200 mg), amiloride (5–20 mg), furosemide (5–80 mg), propanolol (20–480 mg) timolol maleate (5–60 mg), 5 methyldopa (65–2000 mg), felodipine (5–60 mg), nifedipine (5–60 mg), and nitrendipine (5–60 mg). In addition triple drug combinations of hydrochlorothiazide (15–200 mg) plus amiloride (5–20 mg) plus angiotnesin II antagonist of this invention (3–200 mg) or hydrochlorothiazide (15–200 mg) plus timolol maleate (5–60 mg) plus an angiotensin II antagonist of this invention (0.5–250 mg) of hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis as necessary to permit divided daily dosage and, the dose will vary depending on the nature and severity of the disease, weight of patient, special diets and other factors.

No unacceptable toxicological effects are expected when compounds of the invention are administered in accordance with the present invention.

The method of this invention of antagonizing angiotensin II receptors in mammals, including humans, comprises administering to a subject in need of such antagonism an effective amount of a compound of Formula (I). The method of this invention of treating hypertension, congestive heart failure, glaucoma, and renal failure comprise administering a compound of Formula (I) to a subject in need thereof an effective amount to produce said activity.

Contemplated equivalents of Formula (I) compounds are compounds otherwise corresponding thereto wherein substituents have been added to any of the unsubstituted positions of the Formula (I) compounds provided such compounds have the pharmaceutical utility of Formula (I) compounds.

The following examples illustrate preparation of compounds and pharmaceutical compositions of this invention. The examples are not intended to limit the scope of this invention as defined hereinabove and as claimed below.

EXAMPLE 1

S-[(2-n-Butyl-1-{(4-carboxyphenyl)methyl}-1H-imidazol-5-5-yl)methyl]-D,L-2-thio-3-(2-thienyl)-propionic Acid (i) 2-Bromo-3-(2-thienyl)propionic Acid Thienylalanine (17.1 g, 0.1 mol) was added to a solution of 40.2 g (0.34 mol) of potassium bromide in 200 ml of 2.5N sulfuric acid. Solid sodium nitrite (10.5 g, 0.15 mol) was added in portions over 45 minutes to the solution which was held at 0°–4° C. The reaction mixture was stirred at 0°–4° C. for 1 hour, and then stirred at 25° C. for 2 hours. The mixture was extracted with ether and the ether extract was washed with water and brine. The organic extract was dried and concentrated. The residue was dissolved in 20 ml of ether and the solution diluted with petroleum ether to the cloud point and then stored at –20° C. for 18 hours. The insolubles were removed by filtration and the solution concentrated to give 20.5 g (87%) of the product as an oil. The product was used in the next step without further purification.

(ii) 2-Mercapto-3-(2-thienyl)propionic Acid

A solution of 7.05 g (0.03 mol) of the bromo acid in 45 ml of dimethylformamide under argon was treated with 8.91 g (0.0315 mol) of the cesium salt of thiobenzoic acid (J. Org. Chem. 51, 3664). The mixture stirred for 18 hours at ambient temperature. The reaction mixture was diluted with 135 ml of ether and washed with water. The ether was dried and then concentrated to give 5.46 g (62%) of an oil whose NMR was consistent with that expected for the 2-benzoylthio product. This oil (3.0 g) was dissolved in 41 ml of 1N ammonia and stirred for 18 hours under argon. After filtration, the pH was adjusted to 1 with 10% hydrochloric acid. The reaction mixture was extracted with ether and the ether extract was washed with water, dried with sodium sulfate, and concentrated to give the product as an oil.

(iii) 2-n-Butyl-5-hydroxymethylimidazole

A mixture of valeramidine methyl ether hydrochloride (250 g, 1.66 mol) and dihydroxyacetone (150 g, 0.83 mol) dissolved in liquid ammonia was allowed to stand overnight at room temperature in a pressure vessel, and then heated at 65° C. for 4 hours at 375 psi. The ammonia was allowed to evaporate, and the residue was dissolved in methanol (3L). The resulting slurry was refluxed with added acetonitrile (1L). The solution was decanted from the solid ammonium chloride while hot. This procedure was repeated, and the combined acetonitrile extracts were treated with charcoal, filtered hot and the filtrate was concentrated in vacuum to give the dark oil, 2-n-butyl-5-hydroxy-methylimidazole (253 g, 1.63 mol, 98%).

(iv) 2-n-Butyl-4-chloro-5-hydroxymethylimidazole

N-Chlorosuccinimide (54.68 g, 0.405 mol) was added in small portions over 15 minutes to a stirred solution of 2-n-butyl-5-hydroxymethylimidazole (50.00 g, 0.324 mol) in a mixture of 580 ml of tetrahydrofuran and 500 ml of 2-methoxyethanol heated in an oil bath at 40°–50° C. under argon. After 2.5 h the mixture was evaporated to dryness. The residue was suspended in 400 ml of water, stirred at 25° C. for 1 h. A tan solid was collected by filtration, washed with water and air dried to give 51.95 g of a mixture consisting of 2-butyl-4-chloro-5-hydroxymethylimidazole and 2-butyl-4,5-10 dichloroimidazole. The dry powder was suspended in 150 ml of ether, stirred for 1 h at room temperature and then filtered to give 29.91 g (49%) of 2-n-butyl-4-chloro-5-hydroymethylimidazole; mp 150°–153° C.

(v) 2-n-Butyl-4-chloro-5-imidazolecarboxaldehyde

A stirred mixture of 2-n-butyl-4-chloro-5-hydroxymethylimidazole (15.00 g, 0.0795 mol) and activated manganese dioxide (40.00 g) in 600 ml of methylene chloride was refluxed for 24 h using a water separator. The mixture was filtered hot through a Celite® pad. The Celite® pad was washed several times with hot methylene chloride. The washings were combined with the filtrate and concentrated in vacuo to give 12.81 g (86%) of the aldehyde as a white solid; mp 97°–98° C.

(vi) 2-n-Butyl-1-[(4-carbomethoxybiphenyl-5-yl) methyl]-4-chloro-5-imidazolecarboxaldehyde A mixture of 2-n-butyl-4-chloro-5-imidazole-carboxaldehyde (2.46 g, 0.0132 mol) and anhydrous potassium carbonate (2.73 g, 0.0198 mol) in 25 ml of dimethyl-formamide was stirred for 15 minutes at 25° C., then a solution of methyl 5-bromomethylphenyl-4-carboxylate (5.63 g, 0.0185 mol) in 5 ml of dimethyl-formamide was added all at once (rinsed in with 2×5 ml dimethylformamide). The mixture was heated in an oil bath at 105° C. for 20 minutes under argon, cooled, and then filtered. The filter cake was washed with ether and combined with the filtrate. The combined organics were washed with four 50 ml portions of water and then brine. The dried (sodium sulfate) filtrate was evaporated in vacuo to give a syrup (6.97 g). The crude product was flash chromatographed |silica gel 60, 230–400 mesh, 776 g, column 9.5 cm O.D., 9:1 cyclohexane/ethyl acetate (2L) to 8:2 cyclohexane/ethyl acetate]to give 4.34 g(80%)of product as a syrup.

(vii) 2-n-Butyl-1-[(4-carbomethoxyphenyl)methyl]-5-imidazolecarboxaldehyde

A solution of 2-n-butyl-1-[(2-carbomethoxyphenyl)-methyl]-4-chloro-5-imidazolecarboxaldehyde (3.05 g, 0.00742 mol), anhydrous potassium acetate (0.66 g, 0.00742 mol) and 10% palladium on carbon (0.73 g) in 100 ml of methanol was hydrogenated at 35 psi for 45 minutes on a Parr shaker. The mixture was filtered through a Celite® pad. The Celite® pad was washed several times with methanol and the combined filtrates evaporated in vacuo to a syrup. The residue was partitioned in an ether/water mixture. The aqueous phase was adjusted to pH 8 with 5% aqueous sodium carbonate, extracted with ether, and the combined ether extracts were washed with water and brine. The dried (sodium sulfate) solution was evaporated to a syrup (2.72 g) consisting mostly of product and some alcohol.

The syrup was dissolved in 50 ml of methylene chloride, 2.5 g of activated manganese dioxide was added and mixture was refluxed for 3 h. The mixture was filtered through a Celite® pad, the Celite® pad washed several times with methylene chloride and the combined filtrates evaporated in vacuo to give 2.64 g (95%) of product, as a syrup.

(viii) 2-n-Butyl-1-[(4-carbomethoxyphenyl) methyl]-5-chloromethyl-1H-imidazole

Method 1

2-n-Butyl-1-[(4-carbomethoxyphenyl)methyl]-1-H-imidazole-5-carboxaldehyde (6.07 g, 0.202 mol) dissolved in 50 ml of methanol was treated portionwise with 0.483 g (0.0128 mol) of sodium borohydride. After several minutes the pH of the mixture was brought to 7 with 10% hydrochloric acid. The mixture was concentrated under vacuum and water was added. The resulting crystals were collected by filtration, washed with water, and dried to give 5.90 g (97%) of the corresponding alcohol; mp 141°–143° C.

Method 2

2-n-Butyl-5-hydroxymethylimidazole (253 g) was treated with acetic anhydride (400 mL) at −15° C. and then was allowed to warm to ambient temperature with stirring, and then stirred an additional 19 hours. The acetic anhydride was evaporated at reduced pressure, the residue taken up in methylene chloride, and the organic phase was washed with 5% sodium bicarbonate solution and water. The extract was dried over sodium sulfate and concentrated to give 323 g (83%) of 1-acetyl-4-acetoxymethyl-2-n-butylimidazole.

This diacetate was N-alkylated by the following procedure. To a solution of triflic anhydride (120 mL, 0.71 mol) in methylene chloride (200 mL) at −78° C. under argon was added a solution of diisopropyl ethylamine (128 mL, 0.73 mol) and 4-carbomethoxy alcohol (0.72 mol) in methylene chloride (350 mL) over a period of 20 minutes. After being stirred an additional 20 minutes at −78° C., this solution is then treated with 1-acetyl-4-acetoxymethyl-2-n-butylimidazole (146 g, 0.61 mol) dissolved in methylene chloride (300 mL) over a 20 minute interval. The mixture is then stirred at ambient temperature for 18 hours and the solvents are evaporated. The residual 2-n-butyl-5-acetoxymethyl-1-(4-carbomethoxyphenyl)methyl-1H-imidazole is used without purification for the hydrolysis of the acetate group.

A crude 2-n-butyl-5-acetoxymethyl-1-(4-carboxymethoxy-phenyl)methyl-1H-imidazole is stirred in methanol. After cooling, the methanol is removed in vacuo, methylene chloride is added, and the organic extract is washed with water, dried and concentrated to give 2-n-butyl-1-(4-carbomethoxyphenyl)-methyl-5-hydroxymethyl-1H-imidazole.

Thionyl chloride (7.5 ml) was added to 1.51 g (0.00499 mol) of the alcohol and the mixture was heated on a steam bath for 45 minutes. Concentration under vacuum gave a syrup which was treated with 30 ml of ether. The ether then removed under vacuum. Repetition of the ether-evaporation cycle twice gave a solid which was taken up in 10 ml of methylene chloride and the solution added to ether to give 1.76 g (99%) of the chloromethyl imidazole hydrochloride; mp 151°–153° C.

(ix) S-[(2-butyl-1-{(4-carbomethoxyphenyl)methyl}-1H-imidazol-5-yl)methyl]-D, L-2-thio-3-(2-thienyl) propionic Acid A solution of 1.50 g (4.2 mmol) of the 5-chloromethylimidazole hydrochloride, 0.99 g (5.2 mmol) of 2-mercapto-3-(2-thienyl)propionic acid, and 4 ml of triethylamine in 10 ml of dimethylformamide was stirred at ambient temperature for 18 hours. The reaction mixture was diluted with water and extracted with ether. The aqueous layer was extracted with ethyl acetate, the ethyl acetate and then organic extract was dried over magnesium sulfate and concentrated. The residue was chromatographed (reverse phase C18 silica, 70% methanol-water) to give 0.355 g of an oil which was dissolved in 5% sodium bicarbonate. The aqueous layer was washed with ether and then the pH was adjusted to 4 with dilute hydrochloric acid. The product was extracted into ethyl acetate. The organic extract was dried over magnesium sulfate and concentrated to give 0.265 g of the title compound isolated as an oil.

(x) S-[(2-n-Butyl-1-{(4-carboxyphenyl)methyl}-1H-imidazol-5-yl)methyl]-D,L-2-thio-3-(2-thienyl) propionic Acid The mono-acid compound hydrolyzed by stirring with 0.9 g of potassium hydroxide in a mixture of 4 ml of ethanol and 3 ml of water at 25° C. for 18 h. The hydrolysis mixture was evaporated to dryness, the residue was dissolved in water and the solution was extracted with ether. The organic extract was made acidic and the resulting solid was collected and washed with water to give a yellow solid; Anal. Caldc. for $C_{23}H_{26}N_2O_4S \cdot \frac{1}{2}H_2O$: C, 59.08; H, 5.82; N, 6.00. Found: C, 59.02; H, 5.67; N, 5.92.

EXAMPLE 2

S-[(2-n-Butyl-1-{(4-carboxyphenyl)methyl}-1H-imidazol-5-5-yl)methyl]-D-2-thio-3-phenylpropionic Acid Following the procedure of Example 1 replacing 2-mercapto-3-(2-thienyl)-propionic acid with methyl D-2-mercapto-3-phenylpropionic acid gave S-[2-Butyl-{1-[{4-carboxyphenyl)methyl}-1H-imidazol-5-yl)]methyl]-D-2-thio-3-phenylpropionic acid hemihydrate; $[\alpha]^{25}$(1, $CH_3OH$) +2.5°, mp 80° C. (shrinks), 120°C. (turns glassy).

EXAMPLE 3

S-[(2-n-Butyl-1-{(4-carboxyphenyl)methyl}-1H-imidazol-5-5-yl)methyl]thioglycolic Acid Following the procedure of Example 1 replacing 2-mercapto-3-(2-thienyl)-propionic acid with methyl thioglycolate gave S-[(2-butyl-1-{(4-carboxyphenyl)-methyl}-1H-imidazol-5-yl)methyl]thioglycolic acid hemihydrate; softens at 125°–130° C.

EXAMPLE 4

S-[(2-n-Butyl-1-{(4-carboxyphenyl)methyl}-1H-imidazol-5-yl) methyl]-3-thiopronionic Acid Following the procedure of Example 1 replacing 2-mercapto-3-(2-thienyl)propionic acid with methyl 2-mercaptopropionate gave S-[(2-butyl-1-{(4-carboxyphenyl)methyl}-1H-imidazol-5-yl)methyl]-3-thiopropionic acid; mp 70° C.

EXAMPLE 5

S-[(2-n-Butyl-1-{(4-carboxyphenyl)methyl}-1H-imidazol-5-5-yl)methyl]mercaptosuccinic Acid Following the procedure of Example 1 replacing 2-mercapto-3-(2-thienyl)propionic acid with dimethyl 2-mercaptosucinic acid gave S-[(2-butyl-1-{(4-carboxyphenyl)methyl}-1H-imidazol-5-yl)methyl] mercaptosuccinic acid; mp 140° C.

EXAMPLE 6

S-[(2-n-Butyl-1-{(4-carboxyphenyl)methyl}-1H-imidazol-5-5-yl)methyl]-L-2-thio-3-phenylpropionic Acid Following the procedure of Example 1 replacing 2-mercapto-3-(2-thienyl)propionic acid 1-phenylalanine S-[(2-butyl-1-{(4-carboxyphenyl)methyl]-1H-imidazol-5-5-yl) methyl)-L-2-thio-3-phenylpropionic acid; $[\alpha]_{25}$ −1.3° (1%, $CH_3OH$), mp 130° C.

EXAMPLE 7

S-[(2-n-Butyl-1-{(4-carboxyphenyl)methyl}-1H-imidazol-5-5-yl)methyl]thiosalicyclic Acid Following the procedure of Example 1 replacing 2-mercapto-3-(2-thienyl)propionic acid methyl 2-mercaptobenzoate S-[(2-n-butyl-1-{(4-carboxyphenyl)-methyl}-2-butyl-1H-imidazol-5-yl)methyl]thiosalicyclic acid; shrinks at 90° C.

EXAMPLE 8

S-[(2-n-Butyl-1-{(4-carboxyphenyl)methyl}-1H-imidazol-5-5-yl)methyl]-4-thiobenzoic Acid Following the procedure of Example 1 replacing 2-mercapto-3-(2-thienyl)propionic acid methyl 4-mercaptobenzoate S-[(2-n-butyl-1-{(4-carboxyphenyl)-methyl}-1H-imidazol-5-yl)methyl]-4-thiobenzoic acid; mp 213°–215° C.

EXAMPLE 9

S-[(2-n-Butyl-1-{(4-carboxyphenyl)methyl}-1H-imidazol-5-5-yl)methyl]-3-thiobenzoic Acid Following the procedure of Example 1 replacing 2-mercapto-3-(2-thienyl)propionic acid methyl 3-mercaptobenzoate S-[(2-n-butyl-1-{(4-carboxyphenyl)-methyl}-1H-imidazol-5-yl)methyl]-3-thiobenzoic acid hydrate; mp 198°–200° C.

EXAMPLE 10

S-[(2-n-Butyl-1-{(4-carboxyphenyl)methyl}-1H-imidazol-5-yl)methyl]-2-mercaptonicotinic Acid Following the procedure of Example 1 replacing 2-mercapto-3-(2-thienyl)propionic acid methyl 2-mercaptonicotinate S-[(2-n-butyl-1-{(4-carboxyphenyl)-methyl}-1H-imidazol-5-yl)methyl]-2-mercaptonicotinic acid; mp 155°–157° C.,

EXAMPLE 11

S-[(2-n-Butyl-1-{(4-carboxyphenyl)methyl}-1H-imidazol-5-5-yl)methyl]-2-thiomidazole Following the procedure of Example 1 replacing 2-mercapto-3-(2-thienyl)propionic acid 2-mercaptoimidazole S-[(2-n-butyl-1-{(4-carboxyphenyl) methyl}-1H-imidazol-5-5-yl)methyl]-2-thioimidazole; mp 142°–144° C.

EXAMPLE 12

S-[(2-n-Butyl-1-{(4-carboxyphenyl)methyl}-4-chloro-1H-imidazol-5-yl)methyl]thiosalicyclic Acid Following the procedure of Example 1 using 2-n-butyl-1-[(4-carboxymethoxy)phenyl)methyl-4-chloro-5- chloromethylimidazole and methyl 2-mercaptobenzoate gave S-[(2-n-butyl-1-{(4-carbomethoxyphenyl)methyl-4-chloro-1H-imidazol-5-yl)methyl]thiosalicyclic acid; mp 166°–168° C.

EXAMPLE 13

5-[2-n-Butyl-1-{(4-carboxyphenyl)methyl}-1-H-imidazol-5yl]-4,6-dithianonane-1,9-dioic Acid A solution of 1.05 g (0.0035 mol) of 2-n-butyl-1-[(4-carboxyphenyl)-methyl]-1H-imidazole-5-carboxaldehyde and 0.88 g (0.00734 mol) of methyl 3-mercaptopropionate in 50 ml of methylene chloride at 0° C. was treated with 0.992 g (0.007 mol) of boron trifluoride etherate. The reduced mixture was stirred for 30 minutes. The solution was then washed in turn with water, 5% sodium bicarbonate, and water. Drying and concentration gave an oil which on chromatography (silica, 80% ethyl acetate-hexane) gave two components, one of which was converted into the other on thin layer chromatography. This component was dissolved in ethyl acetate and stirred in the presence of silica for 72 hours. Filtration and concentration under vacuum gave more of the product which was combined with the previous fraction to give 1.24 g (68%) of white crystals. The trimethyl ester of the title compound was stirred for 18 hours in a solution of 0.766 g (0.0137 mol) of potassium hydroxide in 60% aqueous ethanol. The mixture was diluted with water and extracted with ether. The aqueous layer was brought to pH 4 with dilute hydrochloric acid. This gave a solid from which the solution was decanted, and the solid was washed several times with water. The resulting solid was triturated with acetonitrile and the resulting insoluble product was purified by chromatography (reverse phase C18, 50% aqueous methanol) colorless crystals; Anal. Calcd. for $C_{22}H_{28}N_2O_6 S_2 \cdot H_2O$: C, 53.00; H, 6.06; N, 5.62. Found: C, 53.23; H, 6.19; N, 5.22.

EXAMPLE 14

S-[(2-n-Butyl-1-{(4-carboxyphenyl)methyl}-1H-imidazol-5-5-yl)methyl]-mercaptoacetic Acid (i) 4-Bromo-2-n-butylimidazole A solution of 20 g (0.16 mol) of 2-n-butylimidazole in 1.2 L of carbon tetrachloride was treated with 57.2 g (0.32 mol) of N-bromosuccinimde and heated with good stirring at 60° for 18 h. Then an additional 10 g of N-bromosuccinimide was added and the heating continued for 4 hours. The solids were collected by filtration. Evaporation of the filtrate gave 15 g of an oily solid which was mostly 2-n-butyl-4,5-dibromoimidazole. Evaporation of the solution obtained by trituration of the initial solids with methylene chloride and concentration gave additional product which was chromatographed over silica (20% ethyl acetate in hexane) to give, when combined with the first fraction, 34.2 g (76%) of dibromo product. A solution of 33.5 g (0.119 mol) of this product in 250 ml of n-propanol was refluxed for 18 hours with a suspension of 100 g (0.794 mol) of sodium sulfite. An additional 50 g of sodium sulfite was added and the mixture refluxed an additional 20 hours. The reaction mixture was concentrated under vacuum. 800 ml of water was added, and then the product was extracted into ether at pH 8. The ether layer was washed with water and brine, dried over sodium sulfate, and concentrated to give 23 g of a solid. Chromatography of the crude product (silica gel, 15–30% ethyl acetate-hexane) gave 7.51 g (31%) of pure 2-n-butyl-4-bromoimidazole. On TLC (silica gel, 20% ethyl acetate in hexane) the dibromo imidazole had an R of =0.55 and was visible under short wavelength uv; the monobromo had an R of 0.25, was not visible under uv, but became visible when exposed to iodine vapor.

(ii) 5-Bromo-2-n-butyl-4-nitroimidazole

A solution of 7.51 g (37 mmol) of 4-bromo-2-n-butylimidazole in 50 ml of anhydrous methanol was treated with total of 3.1 ml of 70% nitric acid to obtain the nitrate salt. The solvents were evaporated under vacuum and dried by successive additions of toluene followed by concentration under vacuum. The residue was taken to −70° C., treated with 30 ml of concentrated sulfuric acid, and slowly warmed to 70° C. The reaction mixture was held at 70° C., for 1 hour. The solution was poured into 800 ml of an ice-water mixture to give a white solid which was collected by filtration and washed with water to give 8.32 g (90.6%) of crystals, $R_f$ 0.26 (silica, 20% ethyl acetate in hexane, weak iodine stain).

(iii) 5-Bromo-2-n-butyl-1-(4-carbomethoxyphenyl)-4-nitro-1H-imidazo]

Anhydrous powdered potassium carbonate (10.12 g, 73 mmol) was added to a solution of 8.26 g (33.3 mmol) of 5-bromo-2-n-butyl-4-nitroimidazole in 60 ml of dry dimethylformamide. The reaction mixture was stirred at 60° C. for 45 minutes. A solution of 8.8 g (36.8 mmol) of methyl 4-bromomethybenzoate in 15 ml of dry dimethylformamide was added dropwise and the mixture stirred at 100°–105° C. for 1.5 hours. The reaction mixture was poured into 700 ml of water and extracted with ethyl acetate several times. The combined organic extracts were washed with water and brine, and then dried over sodium sulfate. Evaporation of the solvent gave 14.4 g of a thick oil which on chromatography (600 ml silica gel, 12.5–20% ethyl acetate in hexane) gave the title compound $R_f$ 0.51 (silica, 2:3 ethyl acetate-hexane).

(iv) S-[(2-n-butyl-1-{(4-carboxyphenyl)methyl}-1H-imdazole-5-yl]mercaptoacetic Acid A solution of di-isopropylamine (0.7 ml, 0.005 mol) in 20 ml of tetrahydrofuran at −78° C. was treated with butyl lithium (2 ml, 2.5N, 0.005 mol) and stirred for 0.5 h. Methyl thioglycolate (1 ml, 0.010 mol) was added and the mixture stirred for 0.25 h and warmed slightly to give a clear solution. A solution of 1.98 g (0.005 mol) of the above bromonitro imidazole in 12 ml of tetrahydrofuran was added at −78° C. The mixture was allowed to warm to 25° over 0.75 h, and then heated at reflux for 0.5 h. The reaction mixture was filtered and the filter cake washed with ethyl acetate. The combined filtrates were concentrated and the residue chromatographed (silica gel, 20–30% ethyl acetate in hexane) to give the nitrosulfide.

A mixture of 0.88 g (2.09 mmol) of the nitrosulfide, 2 g (11.5 mmol) of sodium hydrosulfite, 20 ml of water and 30 ml of ethanol was refluxed for 18 h. The reaction mixture was poured into water, made basic with ammonium hydroxide, and extracted with methylene chloride. The methylene chloride extract was washed with water, dried over sodium sulfate, and concentrated to give the amino sulfide.

The amino sulfide (0.29 g, 0.74 mmol) was dissolved in a mixture of 1 ml of 12N hydrochloric acid, 1 ml of 50% hypophosphorous acid, and 2 ml of water. The reaction mixture was stirred at 0° C. for 10 minutes and then a solution of 0.10 g (1.5 mmol) of sodium nitrite in 2 ml of water was added. The mixture was stirred in the cold for 10 minutes. Extraction of the reaction mixture with methylene chloride followed by chromatography (20–50% ethyl acetate-hexane, silica gel) gave the deaminated sulfide.

A solution of 0.10 g (0.266 mmol) of the diester sulfide in 2 ml of tetrahydrofuran and 0.7 ml of methanol was treated with 0.58 ml (0.584 mol) of 1N sodium hydroxide and stirred at 25° for 2.5 hours and then 0.58 ml of 1N hydrochloric acid was added and the mixture concentrated to dryness. Repetition of the hydrolysis for 18 hours followed by neutralization and extraction with ethyl acetate gave the di-acid which was recrystallized from a mixture of ethyl acetate, ethanol, and hexane; mp 170°–172° C.

EXAMPLE 15

S-[(2-n-Butyl-1-{(4-carboxyphenyl)methyl}-1H-imdazole-5-yl]thiosalicylic Acid

Following the procedure of Example 14 starting with 5-bromo-2-n-butyl-1-(4-carbomethoxyphenyl)methyl]-4-nitro-1H-imidazole and methyl 2-mercaptobenzoate gave S-[(2-n-butyl-1-{(4-carboxyphenyl)methyl}-1H-imidazol-5-5-yl)thiosalicylic acid; mp 260°–262° C. (ethyl acetate-hexane).

EXAMPLE 16

S-[-(2-n-butyl-1-{(4-carboxyphenyl]methyl}-1H-imidazol-5-yl)ethyl]thiosalicyclic Acid (i) 2-n-Butylimidazole-4-acetic Acid. Ethyl Ester Sodium hydride (2.82 g, 0.117 mol) was dissolved in 30 ml of absolute ethanol at 0° C. Valeramidine hydrochloride (16.71 g, 0.123 mol) was added to this solution, and after 15 minutes the solution was filtered and the collected solid was washed with 20 ml of ethanol and 50 ml of benzene. The combined filtrates were diluted with 750 ml of benzene, 15 g (0.117 mol) of methyl 3-formylacrylate was added, and the mixture was refluxed for 18.5 h using a trap to remove water. The solvents were removed under vacuum and the residue slurried in ether. Evaporation of the ether solution gave the title compound as an oil.

(ii) 2(2-n-Butylimidazol-4-yl)ethanol

A solution of 2 g (9.5 mmol) of the above ethyl ester in 50 ml of tetrahydrofuran was added to a suspension of 0.76 g (20 mmol) of lithium aluminum hydride in 50 ml of tetrahydrofuran. After stirring for 2 hours, 3 ml of water was added dropwise, the solution was stirred for 18 hours, and then 1 ml of 10% aqueous sodium hydroxide and 3 ml of water was added. After stirring for ½ hour, the mixture was filtered, the filter cake was washed with tetrahydrofuran, and the combined filtrates were concentrated under vacuum. Chromatography (silica gel, 5–10% methanol in ethyl acetate) gave the product as an amber oil.

(iii) 5(2-Acetoxyethyl)-2-n-butyl-(4-carbomethoxyphenyl)methyl]-1H-imidazole

A solution of 1.37 g (8.1 mmol) of 2-(2-n-butylimidazol-4-yl)ethanol in 20 ml of acetic anhydride was allowed to stand for 18 hours, refluxed for 0.5 hours, and then stored for 72 hours. The solution was concentrated under vacuum, the residue was successively 3 times dissolved in a mixture of toluene and hexane, and then it was concentrated to dryness. The resulting residue 1.69 g (85%) of 1-acetyl-4-(2-acetoxyethyl)-2-butylimidazole.

A solution of trifluoromethanesulfonic anhydride (2.27 g, 8.04 mmol) in 5 ml of methylene chloride at −78° C. was treated with a solution of 1.34 g (8.04 mmol) of methyl 4-hydroxymethylbenzoate and 1.13 g (8.7 mmol) of diisopropylethylamine in 10 ml of methylene chloride. After stirring for 5 hour, the above diacetyl imidazole derivative dissolved in 10 ml of methylene chloride was added dropwise. The temperature was allowed to rise to 25° cover an 18 hour period. The reaction mixture was then washed twice with 5% sodium bicarbonate, dried over sodium sulfate, and concentrated under vacuum. The residue was chromatographed (silica gel, 80–100% ethyl acetate-hexane) to give the title compound as an oil.

(iv) 2-n-Butyl-1-[(4-carbomethoxyphenylmethyl)methyl]-5-(2-chloroethyl)-1H-imidiazole A solution of the above diester (1.35 g, 3.77 mmol) in 2 ml of water and 12 ml of methanol was stirred at ambient temperature for 2 h and then diluted with ethyl acetate. After filtration the filtrate was washed with water, dried over magnesium sulfate, and concentrated under vacuum to give 1.0 g (84%) of an oil which was 2-n-butyl-1-[(4-carbomethoxyphenyl)methyl]-5-(2-hydroxyethyl)-1H-imidazole. This was dissolved in 10 ml of thionyl chloride and refluxed for 2 h and then volatiles were removed under vacuum. The residue was treated with a mixture of toluene and hexane and the solvents evaporated 3 times and hexane and the solvents evaporated 3 times in succession. The title compound was isolated as an oil.

(v) S-[2-(2-n-butyl-1{(4-carboxyphenyl) methyl}-1H-imidazol-5-yl)ethyl]thiosalicylic Acid Methyl thiosalicylate (0.323 g, 1.92 mmol) was added to a suspension of 0.046 g (1.92 mmol) sodium hydride in 1 ml of dimethylformamide. The suspension was stirred until it became clear, then a solution of the above chloride hydrochloride in 2 ml of dimethylformamide wets added and the mixture stirred at ambient temperature for 18 h, followed by heating at 90° for 5 hr. The mixture was poured into water, and extracted with ethyl acetate. The organic layer was washed with water, dried, and concentrated to give an oil which was chromatographed (silica gel, 80% ethyl acetate-hexane) to give the bis ester.

A solution of the bis ester (0.13 g, 0.66 mmol) in a mixture of 4 ml of tetrahydrofuran, 2 ml of methanol, and 1.5 ml (1.48 mmol) of 0.9861N sodium hydroxide was stirred for 18 h. The mixture was neutralized with 1.46 ml of 1N hydrochloric acid and chilled and the resulting crystals were collected by filtration, washed with water, and dried to give off-white crystals; mp 293°–295° C.

EXAMPLE 17

4-[(2-n-Butyl-5-{[(2-carboxyphenyl) thio]methyl}-1-imidazol-5-yl)methyl]-1-naphthalenecarboxylic Acid (i) 2-n-Butyl-5-hydroxymethyl-4-iodoimidazole N-iodosuccinimide (148.75 g, 0.661 mol) was added to a stirred solution of 2-n-butyl-4-hydroxymethylimidazole (100.78 g, 0.652 mol) in 500 ml of absolute ethanol. After 20 minutes the solution was heated to 40°–45° C. for 45 minutes, diluted with 2.5 L of water, and chilled. The crystalline product which formed was collected by filtration, washed with water, and dried to give 1.74.5 g (95%) of crystals; mp 166°–166.5° C.

(ii) 2-Butyl-4-iodoimidazole-5-carboxaldehyde

A stirred mixture of 174.1 g (0.62 mol) of 2-n-butyl-5-hydroxymethyl-4-iodoimidazole and 360 g (4.14 mol) of manganese dioxide in 3 L of dichloromethane was refluxed for 24 hr using a trap to remove water. The hot reaction mixture was filtered through a Celite® pad which was then washed with 4.5 L of boiling methylene chloride. The combined filtrates were concentrated to dryness. The residue was dissolved twice in 150 ml of methanol and each time the solution was concentrated to dryness. The residue was dissolved in 130 ml of methanol and chilled. After crystallization stopped, 700 ml of water was added slowly. The mixture was chilled, and the solid was collected by filtration, washed with water and dried to give 145.2 g (84%) of product; mp 104°–105° C.

(iii) Methyl 4-[(2-n-Butyl-5-formyl-4-iodo-1H-imidazol-5-yl)methyl]-1-napthalene carboxylate A suspension of 29.53 g (0.214 mol) of powdered potassium carbonate, 60.00 g (0.214 mol) of 2-butyl-4-iodoimidazole-5-carboxaldehyde, and 65.68 g (0.235 mol) of methyl 4-bromomethylnaphthalene-1-carboxylate (E. A. Dixon, A. Fischer, and F. P. Robinson, Can. J. Chem. 59, 2629 (1981)) in 600 ml of dimethylformamide was stirred for 5 hours under argon at 70° C. An additional 6.56 g (0.0235 mol) of the bromomethyl ester was added and the suspension was stirred an additional 15 hours at 70° C. The mixture was poured into water and the solid which separated was collected by filtration, washed with water, and triturated several times with 250 ml of boiling methanol to give 86.8 g (85%) of a solid; mp 177.5°–179° C.

(iv) Methyl4-[(2-n-Buty-5-formyl-1H-imidazol-5-5-yl)methyl]-1-naphthalene carboxylate A suspension of 40.0 g (83.0 mmol) of the iodo aldehyde, 9.07 g (92.4 mmol) of potassium acetate, and 6.0 g of 10% palladium on carbon in 1.2 liters of ethyl acetate was shaken under hydrogen in a Parr apparatus for 2 hours. The solids were removed by filtration and an additional 8.0 g of 10% palladium on carbon and 9.07 g (92.4 mmol) of potassium acetate were added. After an additional 2 hours of shaking under hydrogen, the solids were again removed by filtration and the solution concentrated to about ⅓ volume. The ethyl acetate solution was washed with aqueous sodium carbonate, dried over magnesium sulfate, and concentrated under vacuum to give an oil which crystallized. Recrystallization from a methylene chloride-hexane mixture gave 25.77 g (87.6%) of colorless crystals; mp 95.5°–97° C.

(v) Methyl 4-[(2-n-Butyl-5-{[(2-carbomethoxyphenyl)-thio]methyl]-1-naphthalenecarboxylate The title compound was prepared following the procedure of Example 1 (viii–ix)replacing 2-n-butyl-1-[(4-carbomethoxyphenyl)methyl-1H-imidazole-5-carboxaldehyde with methyl 4-[(2-n-butyl-5-formyl-1H-imidazol-5-yl)methyl]-1-naphthalene carboxylate and replacing 2-mercapto-3-(2-thienyl)propenoic acid with methyl 2-mercaptobenzoate; mp 130°–132° C.

(vi) 4-[(2-n-Butyl-5-{[(2-carboxyphenyl)thio]methyl}-H-imidazol-5-yl)methyl]-1-naphthalenecarboxylic Acid The title compound was prepared following the procedure of Example (x); mp 272°–274° C.

EXAMPLE 18

S-[(2-n-Butyl-1-{(4-carboxyphenyl)methyl}-1H-5-yl)methyl]thiolactic Acid

The title compound was prepared following the procedure of Example 1 replacing 2-mercapto-3-(2-thienyl)propionic acid with ethyl thiolactate; mp 97° C. (D).

EXAMPLE 19

S-[(2-n-Butyl-1-{(4-carboxyphenyl)methyl}-4-nitro-1H-imidazol-5-yl)methyl]mercaptoacetic Acid The title compound was prepared as an amorphous solid following the procedure of Example 14, except the nitro-reducing and deaminating steps in subsection (iv) were not carried out; Anal. Calcd. for $C_{17}H_{19}N_3O_6S$: C, 51.90; H, 4.86; N, 10.68. Found: C, 52.00; H, 5.16; N, 10.06.

EXAMPLE 20

S-[(2-n-Butyl-1-{(4-carboxyphenyl)methyl}-4-nitro-1H-imidazol-5-yl)methyl]thiosalicylic Acid The title compound was prepared following the procedure of Example 14, except the nitro-reducing and deaminating steps in subsection (iv) were not carried out and methyl thioglycolate was replaced by methyl 2-mercaptobenzoate; mp 246°–247° C.

EXAMPLE 21

S-[(2-n-Butyl-1-{(4-carboxyphenyl)methyl}-4-nitro-1 H-imidazol-5-yl)methyl]-L-2-thio-3-phenylpropionic Acid The title compound was prepared following the procedure of Example 14, except the nitro-reducing and deaminating steps in subsection (iv) were not carried out and methyl thioglycolate was replaced by L-phenylalanine; mp 105°–107° C.

EXAMPLE 22

An oral dosage form for administering orally active Formula (I) compounds is produced by screening, mixing and filling into hard gelatin capsules the ingredients in proportions, for example, as shown below.

| Ingredients | Amounts |
|---|---|
| S-[(2-n-butyl-1-{(4-carboxyphenyl)methyl}-1H-imidazol-5-yl)methyl]thiosalicylic acid | 100 mg |
| magnesium stearate | 10 mg |
| lactose | 100 mg |

EXAMPLE 23

The sucrose calcium sulfate dihydrate and orally active Formula (I) compounds are mixed and granulated with a 10% gelatin solution. The wet granules are screened, dried, mixed with the starch, talc and stearic acid, screened and compressed into a tablet.

| Ingredients | Amounts |
|---|---|
| S-[(2-n-butyl-1-{(4-carboxyphenyl)methyl}-1H-imidazol-5-yl)methyl]-2-thio-3-(2-thienyl)propenoic acid | 75 mg |
| calcium sulfate dihydrate | 100 mg |
| sucrose | 15 mg |
| starch | 8 mg |
| talc | 4 mg |
| stearic acid | 2 mg |

EXAMPLE 24

S-[(2-n-butyl-1-{(4-carboxyphenyl)methyl}-1H-imidazol-5-yl)methyl]thiosalicylic acid, 50 mg, is dispersed in 25 mL of normal saline to prepare an injectable preparation.

EXAMPLE 25

A topical ophthalmological solution for administering Formula (I) compounds is produced by mixing under sterile conditions the ingredients in proportions, for example, as shown below.

| Ingredients | Amounts (mg/mL) |
| --- | --- |
| S-[(2-n-butyl-1-{(4-carboxyphenyl)-methyl}-1H-imidazol-5-yl)methyl]-2-mercaptonicotinic acid | 1.0 |
| dibasic sodium phosphate | 10.4 |
| monobasic sodium phosphate | 2.4 |
| chlorobutanol | 5.0 |
| hydroxypropanol methylcellulose | 5.0 |
| sterile water | q.s. ad 1.0 mL |
| 1.0N sodium hydroxide | q.s. ad pH 7.4 |

It is to be understood that the invention is not limited to the embodiments illustrated hereabove and the right to the illustrated embodiments and all modifications coming within the scope of the following claims is reserved.

What is claimed is:

1. The compound which is:

methyl 4-[(2-n-butyl-5-{[(2-carbomethoxyphenyl)-thio]methyl}-1H-imidazol-5-yl)methyl]-1-naphthalenecarboxylate;

S-[(2-n-butyl-1-{(4-carboxyphenyl)methyl}-4-chloro-1H-imidazol-5-yl)methyl]thiosalicylic acid;

S-[(2-n-butyl-1-{(4-carboxyphenyl)methyl}-1H-imidazol-5-yl)methyl]-4-thiobenzoic acid;

S-[(2-n-butyl-1-{4-carboxyphenyl)methyl}-1H-imidazol-5-yl)methyl]-3-thiobenzoic acid;

S-[(2-n-butyl-1-{(4-carboxyphenyl)methyl}-4-nitro-1H-imidazol-5-yl)methyl]thiosalicylic acid;

S-[(2-n-butyl-1-{(4-carboxyphenyl)methyl}-1H-imdazole-5-yl]thiosalicylic acid; or S-[2-n-butyl-1-{(4-carboxyphenyl)methyl}-1H-imidazol-5-yl)ethyl]thiosalicyclic acid; or a pharmaceutically acceptable salt thereof.

2. The compound which is S-[(2-n-butyl-1-{(4-carboxyphenyl)methyl}-1H-imidazol-5-yl) methyl]-thiosalicylic acid or a pharmaceutically acceptable salt thereof.

3. The compound which is S-[(2-n-butyl-1-{(4-carboxyphenyl)methyl}-1H-imidazol-5-yl)methyl]-2-mercaptonicotinic acid or a pharmaceutically acceptable salt thereof.

4. The compound which is 4-[(2-n-butyl-5-{[(2-carboxyphenyl)thio]methyl}-1H-imidazol-5-yl)methyl]-1-naphthalenecarboxylic acid or a pharmaceutically acceptable salt thereof.

5. The compound which is S-[(2-n-butyl-1-{(4-carbomethoxyphenyl)methyl}-1H-imidazol-5-yl)methyl]-2-thioimidazole or a pharmaceutically acceptable salt thereof.

* * * * *